(12) United States Patent
Jones et al.

(10) Patent No.: US 10,675,412 B2
(45) Date of Patent: Jun. 9, 2020

(54) PISTON SEAL

(75) Inventors: Anthony Jones, Oxford (GB); Jonathan Upsdell, Oxford (GB)

(73) Assignee: Oxford Nanopore Technologies Limited, Oxford (GB)

( * ) Notice: Subject to any disclaimer, the term of this patent is extended or adjusted under 35 U.S.C. 154(b) by 884 days.

(21) Appl. No.: 14/344,463

(22) PCT Filed: Sep. 11, 2012

(86) PCT No.: PCT/GB2012/052234
§ 371 (c)(1),
(2), (4) Date: Jul. 28, 2014

(87) PCT Pub. No.: WO2013/038164
PCT Pub. Date: Mar. 21, 2013

(65) Prior Publication Data
US 2014/0377108 A1   Dec. 25, 2014

(30) Foreign Application Priority Data

Sep. 15, 2011 (GB) .................................. 1116019.9
Sep. 15, 2011 (GB) .................................. 1116020.7

(51) Int. Cl.
*A61M 5/315* (2006.01)
*B29L 31/00* (2006.01)
(Continued)

(52) U.S. Cl.
CPC ..... *A61M 5/31513* (2013.01); *A61M 5/31515* (2013.01); *A61M 2205/0222* (2013.01);
(Continued)

(58) Field of Classification Search
CPC ......... A61M 2005/31521; A61M 2005/31516; A61M 5/31511; A61M 5/31513;
(Continued)

(56) References Cited

U.S. PATENT DOCUMENTS 1,955,157 A   4/1934 Wayne
2,461,211 A   2/1949 Guthrie
(Continued)

FOREIGN PATENT DOCUMENTS

CH   344883   2/1960
CN   101224320   7/2008
(Continued)

OTHER PUBLICATIONS

International Search Report and Written Opinion for Application No. PCT/GB2012/052234, 13 pages, dated Nov. 4, 2013.
(Continued)

*Primary Examiner* — F Daniel Lopez
*Assistant Examiner* — Michael Quandt
(74) *Attorney, Agent, or Firm* — Wolf, Greenfield & Sacks, P.C.

(57) ABSTRACT

A piston head for a syringe pump comprises a barrier portion (11) for driving fluid through a syringe pump barrel (30), wherein a peripheral section (13,14) of the barrier portion (11) is shaped to seal against the syringe pump barrel (30); and a re-silent member (15) arranged to resist deformation of the shaped peripheral section (13,14) of the barrier portion (11).

10 Claims, 2 Drawing Sheets

(51) Int. Cl.
  *F16J 15/328* (2016.01)
  *F16J 15/3208* (2016.01)
  *B29L 31/26* (2006.01)
  *F04B 53/14* (2006.01)

(52) U.S. Cl.
  CPC ...... *A61M 2207/00* (2013.01); *B29L 2031/26* (2013.01); *B29L 2031/7544* (2013.01); *F04B 53/143* (2013.01); *F16J 15/328* (2013.01); *F16J 15/3208* (2013.01)

(58) Field of Classification Search
  CPC .............. A61M 5/31515; F16J 15/3208; F16J 15/3204; F16J 15/328; F16J 1/003; F16J 1/006; F16J 1/008; F16J 1/001; F04B 53/143
  USPC .................................. 92/240, 241, 249, 254
  See application file for complete search history.

(56) References Cited

U.S. PATENT DOCUMENTS

| | | | |
|---|---|---|---|
| 2,756,748 | A | 7/1956 | Ferguson |
| 2,857,184 | A * | 10/1958 | Mancusi, Jr. ........ F16J 15/3204 277/468 |
| 3,270,771 | A | 9/1966 | Luke et al. |
| 3,422,848 | A | 1/1969 | Liebman et al. |
| 3,799,411 | A | 3/1974 | Carpenter |
| 4,435,173 | A | 3/1984 | Siposs et al. |
| 4,712,583 | A | 12/1987 | Pelmulder et al. |
| 5,496,009 | A | 3/1996 | Farrell et al. |
| 5,529,280 | A | 6/1996 | Satoh et al. |
| 5,771,935 | A | 6/1998 | Myers |
| 5,800,405 | A | 9/1998 | McPhee |
| 5,902,276 | A * | 5/1999 | Namey, Jr. ......... A61M 5/31511 604/218 |
| 6,004,300 | A | 12/1999 | Butcher et al. |
| 6,067,864 | A | 5/2000 | Peterson |
| 6,090,081 | A * | 7/2000 | Sudo ................. A61M 5/31513 604/218 |
| 6,254,057 | B1 | 7/2001 | Pubben et al. |
| 6,537,451 | B1 | 3/2003 | Hotier |
| 6,565,535 | B2 | 5/2003 | Zaias et al. |
| 7,111,848 | B2 * | 9/2006 | Tachikawa ......... A61M 5/31513 277/535 |
| 7,360,556 | B2 | 4/2008 | Mijers |
| 7,537,437 | B2 | 5/2009 | Muramatsu et al. |
| 7,682,356 | B2 * | 3/2010 | Alessi ................. A61K 9/0004 604/222 |
| 7,766,028 | B2 | 8/2010 | Massengale et al. |
| 8,123,756 | B2 | 2/2012 | Miller et al. |
| 8,162,006 | B2 | 4/2012 | Guala |
| 8,312,805 | B1 * | 11/2012 | Blume ................. F04B 53/143 277/560 |
| 9,194,504 | B2 | 11/2015 | Cormier et al. |
| 9,551,338 | B2 | 1/2017 | Jones et al. |
| 9,593,370 | B2 | 3/2017 | Jones |
| 10,036,065 | B2 | 7/2018 | Jones |
| 10,054,234 | B2 | 8/2018 | Jones et al. |
| 10,342,589 | B2 | 7/2019 | Jones et al. |
| 2001/0035516 | A1 | 11/2001 | Nichols et al. |
| 2002/0007139 | A1 | 1/2002 | Zaias et al. |
| 2003/0116206 | A1 | 6/2003 | Hartshorne et al. |
| 2005/0227239 | A1 | 10/2005 | Joyce |
| 2006/0069356 | A1 * | 3/2006 | Witowski ........... A61M 5/31511 604/222 |
| 2006/0105461 | A1 | 5/2006 | Tom-Moy et al. |
| 2006/0210995 | A1 | 9/2006 | Joyce |
| 2007/0163656 | A1 | 7/2007 | Mijers |
| 2007/0202008 | A1 | 8/2007 | Schembri et al. |
| 2007/0219508 | A1 | 9/2007 | Bisegna et al. |
| 2008/0003147 | A1 | 1/2008 | Miller et al. |
| 2008/0032290 | A1 | 2/2008 | Young |
| 2009/0311117 | A1 | 12/2009 | Gustafsson |
| 2010/0062446 | A1 | 3/2010 | Hanafusa |
| 2010/0070069 | A1 | 3/2010 | Hofstadier et al. |
| 2010/0113762 | A1 | 5/2010 | Ball et al. |
| 2010/0148126 | A1 | 6/2010 | Guan et al. |
| 2011/0108147 | A1 | 5/2011 | Carmody et al. |
| 2012/0322679 | A1 | 12/2012 | Brown et al. |
| 2013/0203634 | A1 | 8/2013 | Jovanovich et al. |
| 2013/0217106 | A1 | 8/2013 | Jones |
| 2014/0238497 | A1 | 8/2014 | Jones et al. |
| 2014/0314594 | A1 | 10/2014 | Jones et al. |
| 2015/0031020 | A1 | 1/2015 | Jayasinghe et al. |
| 2017/0321694 | A1 | 11/2017 | Jones et al. |
| 2017/0327880 | A1 | 11/2017 | Jones |
| 2019/0032798 | A1 | 1/2019 | Jones et al. |
| 2019/0282284 | A1 | 9/2019 | Jones et al. |

FOREIGN PATENT DOCUMENTS

| | | |
|---|---|---|
| CN | 201152237 | 11/2008 |
| DE | 202004009831 | 8/2004 |
| DE | 102006026220 B4 | 12/2007 |
| DE | 202007012680 | 1/2008 |
| DE | 102009006203 A1 | 4/2010 |
| EP | 0015144 A1 | 9/1980 |
| EP | 0086073 | 8/1983 |
| EP | 0247824 | 12/1987 |
| EP | 0925798 B1 | 6/1999 |
| EP | 0934757 | 8/1999 |
| EP | 1197693 | 4/2002 |
| EP | 1351183 A2 | 10/2003 |
| EP | 1544310 A2 | 6/2005 |
| EP | 1640168 | 3/2006 |
| EP | 1946793 | 7/2008 |
| EP | 2165723 A1 | 3/2010 |
| FR | 2947873 A1 | 1/2011 |
| GB | 840499 | 7/1960 |
| GB | 896056 | 5/1962 |
| GB | 2443260 | 4/2008 |
| GB | 2447043 | 9/2008 |
| GB | 2474073 | 4/2011 |
| JP | 6-319801 | 11/1994 |
| JP | 2003-235974 | 8/2003 |
| JP | 2003-328420 | 11/2003 |
| JP | 2009-66599 | 4/2009 |
| WO | 81/01445 A1 | 5/1981 |
| WO | WO 03/017020 | 2/2003 |
| WO | 2005/005829 A1 | 1/2005 |
| WO | WO 2005/017356 A1 | 2/2005 |
| WO | WO 2005/124888 | 12/2005 |
| WO | 2007/054233 A1 | 5/2007 |
| WO | 2007/102836 A1 | 9/2007 |
| WO | WO 2007/141058 A1 | 12/2007 |
| WO | WO 2008/008974 | 1/2008 |
| WO | WO 2008/111863 | 9/2008 |
| WO | WO 2009/020682 A2 | 2/2009 |
| WO | WO 2009/077734 A2 | 6/2009 |
| WO | WO 2010/083147 | 7/2010 |
| WO | WO 2011/067559 | 6/2011 |
| WO | WO 2012/042226 | 4/2012 |

OTHER PUBLICATIONS

Great Britain Search Report for Application No. GB1116020.7, 2 pages, dated Jan. 12, 2012.
Great Britain Search Report for Application No. GB1116019.9, 2 pages, dated Aug. 2, 2012.
Boresi et al., Advanced mechanics of materials. 6th edition. 2003. Chapter 13. 457-501.
U.S. Appl. No. 16/018,758, filed Jun. 26, 2018, Jones et al.
U.S. Appl. No. 16/410,798, filed May 13, 2019, Jones et al.

* cited by examiner

PISTON SEAL

RELATED APPLICATIONS

This application is a 35 U.S.C. 371 national stage filing of International Application No. PCT/GB2012/052234, filed on Sep. 11, 2012, which claims priority to Great Britain Application No. 1116020.7, filed on Sep. 15, 2011, and Great Britain Application No. 1116019.9, filed on Sep. 15, 2011. The contents of the aforementioned applications are hereby incorporated by reference.

The present invention relates to sealing a piston against a surround barrel, for example in a syringe or syringe pump and to a syringe pump comprising a piston and a barrel.

Conventional syringes and syringe pumps operate by the motion of a piston or plunger displacing fluid within a barrel. When the plunger is advanced from one end within the barrel, fluid in the barrel is forced out the other end. On the other hand, when the plunger is drawn out of the barrel through one end, fluid is drawn in to the barrel through the other end. To allow this pumping operation to occur properly, the plunger is sealed against the barrel, so that fluid cannot pass around the plunger for example.

One common method of sealing the plunger against the barrel in disposable syringes is by using an elastic seal such as an O-ring. Such an O-ring is provided around the outside of the plunger, close to the end of the plunger driving fluid within the barrel. The O-ring provides a relatively deformable surface that can thus shape itself to the barrel and form a tight seal. As such, the O-ring is positioned between the plunger and the barrel and so is in contact with the fluid in the barrel.

Another method of sealing the plunger against the barrel is for the whole plunger head to be made of an elastic material, so that the plunger head deforms as a whole to produce a seal within the barrel.

In both of these cases, the fluid in the barrel is in contact with the elastic material that is being used to create the seal. This raises possible fluid contamination/interaction issues. In fluidic and microfluidic applications, and biological fluidic applications in particular, it is undesirable to introduce materials into the syringe or syringe pump that might somehow react with the fluids or leach contaminants into the process fluids and somehow affect the experiment being performed.

A yet further approach is to provide a substantially rigid plunger head for use with a deformable barrel such that the barrel deforms to provide a tight seal. However a deformable barrel is not always desirable.

Further, the use of an elastic sealing material causes a characteristic stick/slip jump when first moving the plunger. This is due to high static friction between the elastic sealing material and barrel, which must be overcome to start the plunger moving. The high static friction means a correspondingly large force is required to start moving the plunger, and a characteristic jerk occurs before smooth plunger motion can be observed once enough force has been applied to the plunger to overcome the static friction. Even after the static friction has been overcome, the presence of the elastic O-ring results in a relatively large amount of dynamic friction (and hence a corresponding large required driving force) that must be overcome to keep the plunger moving. This makes fine control of the syringe difficult, especially when first beginning to move the plunger.

Further, it is typical for conventional syringes and syringe pumps to somewhat rely upon deformation of the outer barrel around the piston seal (be it an O-ring or the entire piston head) to achieve a good seal. That is, the barrel will deform slightly outwards in the region of the seal to allow the piston to be moved whilst maintaining pressure on the seal.

An alternative to the elastic material approach is to make the syringe (from metal for example) so the piston is an exact fit for the barrel, the barrel being made, for example of glass. However, this approach is expensive due to the high tolerances required for the barrel and syringe and is therefore not well suited to the mass manufacture of disposable syringes. The use of metal may also introduce fluid contamination considerations.

The present invention aims to provide a syringe pump head that at least partly overcomes some or all of the forgoing problems.

According to a first aspect of the invention, there is provided a piston seal, comprising: a barrier portion for driving fluid; and/or a resilient member arranged to resist deformation of a peripheral section of the barrier portion.

According to this aspect of the invention, a piston seal is provided which provides a long lasting seal. The presence of a resilient member helps maintain the shape of the sealing section of the barrier portion. This allows the seal of the piston to take advantage of the material properties of the resilient member to maintain a good sealing force whilst also utilising the material properties of the barrier portion to create a low friction seal or a seal that does not interact with the pumped fluids for example. Therefore, even if the material of the barrier portion is subject to creep, such that over time it would not provide a good seal by itself, the resilient member continues to resist the deformation and maintains a good seal. As such, a disposable seal can be produced at a reasonable cost whilst also being suitable for fluidic and microfluidic applications. The resilient member preferably has a lower creep than the barrier portion, namely the resilient member has less of a tendency to deform permanently over time under the influence of stress. Preferably the resilient material has substantially no creep.

The peripheral section of the barrier portion can be shaped to form a seal for sealing against a barrel around the piston seal. The barrier portion of the piston seal seals against a surrounding barrel, for example in a syringe or syringe pump, thereby reducing the number of components of the syringe that are in contact with a liquid held in the syringe chamber.

The barrier portion can have a barrier surface for contacting the fluid in the syringe pump, and the resilient member is provided on the opposite side of the barrier portion to the barrier surface. According to this arrangement, the resilient member is isolated from the fluid chamber of the syringe, so that (in use) it does not come into contact with fluid in the syringe. This helps avoid any possibility of the material of the resilient member interacting with the fluid, whether by reaction or leaching contaminants. This means the syringe plunger head (also known as a pump head or piston head) is suitable for uses which require low levels of fluid contamination, such as fluidic and micro fluidic applications, specifically those involving biological materials such as proteins, for example enzymes or biological pores, and lab-on-a-chip applications.

The resilient member can have a maximum width that is smaller than the maximum width of the plunger head, and can be arranged so that it does not contact the syringe pump barrel in use. As a result, the resilient member will not come into contact with the barrel of the syringe. This means the coefficient of friction of the resilient member is irrelevant to the motion of the plunger in the barrel, and the friction characteristics are dictated by the material chosen for the barrier portion.

The peripheral section of the barrier portion can be shaped to form a lip projecting from the barrier portion, optionally around the resilient member. The resilient member can be arranged within the lip to resist inwards deformation of the lip. The inner surface of the lip can comprise an overhang and the resilient member can project beneath the overhang. The outer surface of the lip can have a sealing surface for sealing against a syringe barrel, in use. According to these configurations, the lip provides a section to be deformed and seal against the barrel and simultaneously provides a section through which the resilient member can resist the deformation. The lip can also provide a mechanical restraint to the resilient member, by means of the overhang for example, to keep the resilient member in place. The plunger can further comprise a retaining portion for retaining the resilient member against the lip. This allows for the resilient member to be securely positioned between the lip and the retaining portion.

The lip can have a tip that tapers to reduce in thickness. According to this construction, the tip of the lip, which comes into contact with the barrel, can be thinner than the portion adjoining the main body of the barrier portion. This allows for the hoop stresses in the region of the seal to be reduced, making a more adaptive seal without sacrificing the overall strength of the piston seal.

The resilient member and the barrier portion are preferably made of different materials. The barrier portion and/or retaining portion of the piston seal can be made of a plastics material which provides a low friction sealing surface against the barrel. A low friction plastics material has a coefficient of dynamic friction of 0.4 or less, preferably 0.2 or less as measured relative to steel according to the method of ASTM D1894. The plastics material can comprise or consist of for example, polytetrafluoroethylene, ultra-high-molecular-weight polyethylene, polypropylene, perfluoroalkoxy or fluorinated ethylene propylene, and is preferably an easily mouldable material such as ultra-high-molecular-weight polyethylene.

The resilient member can be a spring or elastomeric material. The elastomeric material can comprise or consist of for example, a rubber, a silicone material, or a thermoplastic elastomer. A thermoplastic elastomer is a preferable material for the resilient member as it allows easy moulding and thus cheap manufacture. It can also produce a good bond to the barrier portion and/or retaining portion. The resilient member is preferably made of a material having a lower elastic modulus than the material of the barrier portion.

According to another aspect of the invention, there is provided a syringe pump comprising the piston seal according to the previous aspect.

The piston seal is flexible which enables the plunger to move freely over any surface irregularities on the inner surface of the barrel that might be present, whilst maintaining a good seal. A surface irregularity may be for example, a small variation in the diameter of the barrel along its length. The ability of the plunger to flex enables the plunger and barrel to be made to lower manufacturing tolerances than might otherwise be required, which in turn lowers the cost of goods. Cost is an important consideration when the syringe pump is intended to be disposable, for example for medical or scientific purposes. The flexibility of the piston seal may in part be due to the flexibility of the resilient member. The barrier portion may also be flexible to some extent.

The ability of the piston seal to flex also enables the use of a rigid barrel. This is particularly advantageous where substantially no deformation of the barrel during normal use is required, namely where it is required that the barrel wall remains stationary.

The barrel may have a feature on its external surface which may cooperate with a moving part. The feature may be a screw thread which cooperates with a complementary screw thread. The piston may comprise the complementary screw thread. The piston may comprise a sheath configured to move around an outer surface of the barrel; wherein an inner surface of the sheath and the outer surface of the barrel have complementary screw threads so that, in use, rotating the piston causes the piston to travel along the barrel. In this particular case, it is preferred that the barrel does not deform substantially such that the complementary screw threads are able to engage with each other properly.

According to another aspect of the invention, there is provided a method of forming a piston seal. The method can comprise: moulding a barrier portion for driving fluid through a syringe pump barrel, wherein a peripheral section of the barrier portion is shaped to seal against the syringe pump barrel; and/or moulding a resilient member arranged to resist deformation of the shaped peripheral section of the barrier portion. The piston seal can be the piston seal of the first aspect. The steps of moulding the barrier portion and moulding the resilient member can be performed as an over-moulding or two-shot moulding process.

The present invention will be described with reference to exemplary embodiments and the accompanying Figures in which.

Figure 1:
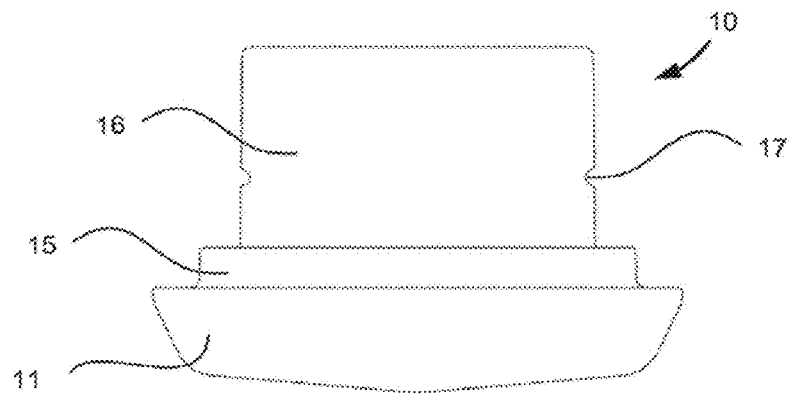
FIG. 1 is schematic diagram of a piston seal.

The present invention has identified that conventional syringe pumps are unsuitable for many fluidic and microfluidic applications. For example, WO 2009/077734 hereby incorporated by reference, relates to the formation of layers of amphiphilic molecules, in which nanopores can be deployed to provide an environment which can be useful, for example, for sequencing polynucleotides. This is an example of a 'nanopore application', referred to below. The formation of the bi-layer, the provision of the nanopores, and the subsequent provision of test fluids require careful control of the fluidic environment, both in mechanical and chemical terms.

For example, when fluids are pumped via a volumetric displacement in the course of creating the bi-layers or performing a test, there is a risk of an unknown amount of air being present within the system. This can be problematic, because the air is compressible and the required volumetric output of liquid is typically small, but required to be accurate. Therefore, if air is being compressed, the change in air volume can be large (in percentage terms) compared to the volume to be pumped, making it difficult for a user to accurately know how much liquid is actually being pumped.

Further, in nanopore applications particularly, the presence of air can directly affect the quality and/or success of an experiment. If bubbles are present in fluid delivered to a nanopore cell, comprising a nanopore positioned in a lipid bi-layer, the bubbles can disrupt the bi-layer and hence the viability of the cell.

Conventional disposable syringes can introduce air into the syringe barrel if the seal is not strong enough to overcome a negative pressure. That is, for example, when the syringe has to actively pull fluid into the barrel against another force, it is possible for the seals of conventional syringes to fail. This can lead to air being drawn into the barrel around the seal, instead of liquid being drawn into the barrel as intended. This results in the unintentional and undesirable introduction of air into the overall fluidics system, which could be problematic later in an experiment as previously discussed.

In the case of pumping lipid to form bi-layers, an extremely slow pumping speed is required. An example range is between 1 µl/s to 0.1 µl/s. The stick/slip issues with conventional elastic-sealing syringe pumps makes control of such flow rates extremely problematic, and can make repeatability of experiments very difficult. This is particularly relevant when considering the small volumes of liquids being displaced and the need to ensure that accurate amounts of a required fluid are provided at the correct time.

Another consideration for nanopore applications is that the presence of contaminants in the system poses a risk of blocking of the nanopores and/or interacting with biological molecules (including the biological nanopores) in an undesirable way. As such, it is desirable to minimise the number of materials in contact with the process fluids and, for those materials that will contact the process fluids, use materials that will have the minimum interaction with the fluids (e.g. exhibiting low binding with the fluids, low leaching of contaminants into the fluids). Contamination is a particular problem with biological nanopores as the pore may be temporarily or permanently deactivated. Also, other proteins in the system may be deactivated or denatured.

Of course, many of the above considerations are not limited to nanopore applications, and are generally applicable to other fluidic and microfluidic environments. Whilst some of these issues could be overcome using, for example, a glass syringe with a plunger that is machined to tightly fit the barrel, such syringes are typically too expensive to be suitable for use in the disposable manner often needed by fluidic and microfluidic environments.

Figure 4:
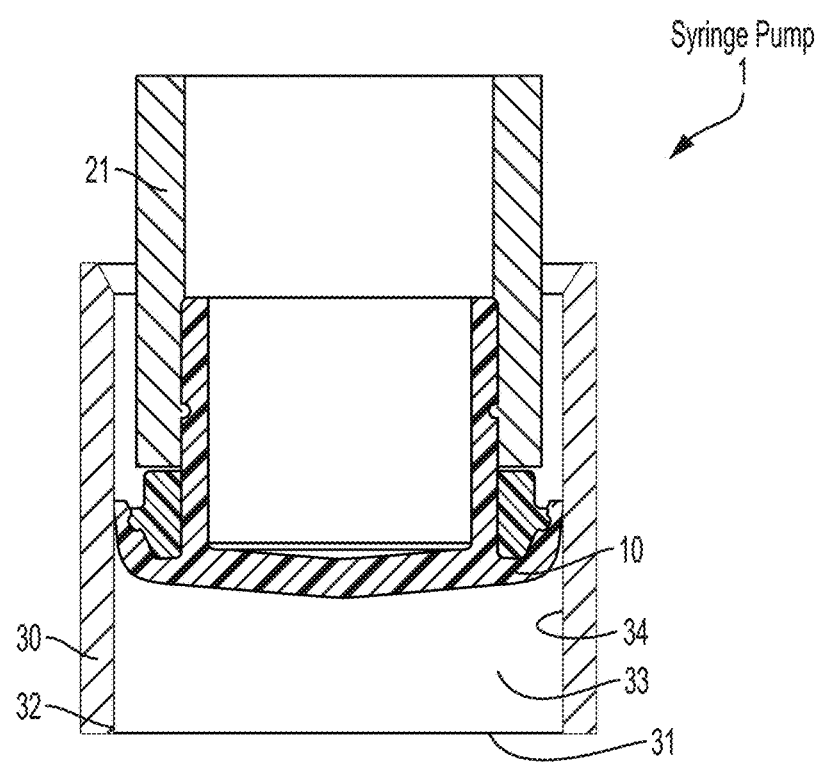
FIG. 4 is a cross-sectional view of a syringe pump incorporating the piston seal depicted in FIG. 1 and a barrel.

The pump 1, depicted in FIG. 4, is a syringe pump. That is, the pumping operation is achieved by the motion of a plunger, or piston, 21 displacing fluid within a barrel 30 in the manner of a syringe.

For fluidics or nanopore applications, the pump 1 may be operable to produce a variety of flow rates. For example, in nanopore applications, it may be desirable for a pump to produce flow rates of from 50 to 100 µl/s for cleaning; for initially priming the fluid lines with the working fluid it may be desirable for a pump to produce flow rates of from 20 to 50 µl/s; for providing lipid for bi-layer formation it may be desirable for a pump to produce flow rates of from 0.1 to 0.5 µl/s; and for providing pores or buffer it may be desirable for a pump to produce flow rates of 1 to 3 µl/s. A single pump may be capable of producing the flow rates for each of these requirements, but individual pumps for each requirement may also be used. In general, it is desirable for the pump 1 to produce flow rates of 0.01 µl/s or more, optionally 0.05 µl/s or more, further optionally 0.1 µl/s or more, still further optionally 20 µl/s or more and still further optionally 50 µl/s or more. Further it may be desirable for the pump 1 to be operable to produce flow rates of 500 µl/s or less, optionally 200 µl/s or less, further optionally 100 µl/s or less, still further optionally 50 µl/s/ and still further optionally 20 µl/s or less.

Figure 3:
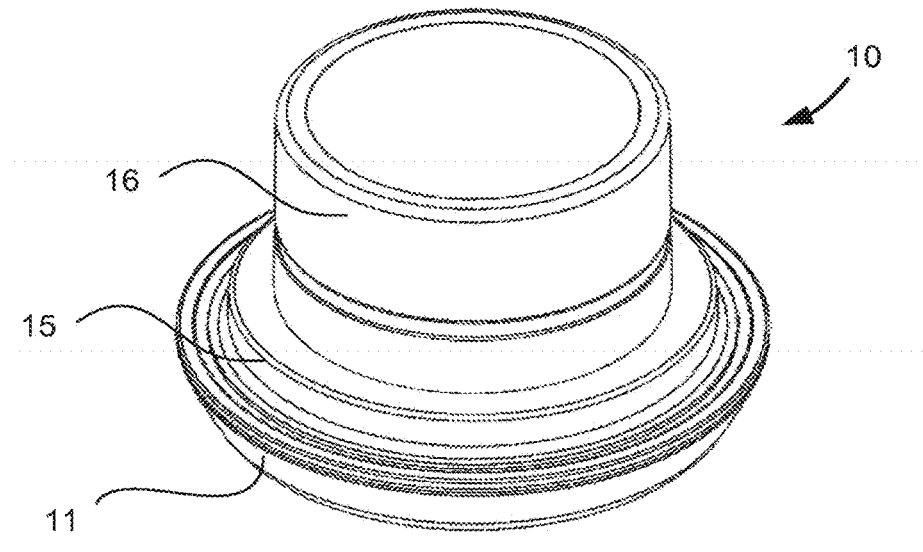
FIG. 3 is a perspective view of the piston seal of FIG. 1.

In the geometry of FIG. 4, the piston/plunger 21 has a head 10 that is circular in cross-section and fits snugly within the cylindrical barrel 30 so that, when the plunger 21 is advanced within the barrel 30 (i.e. moved downwards in FIG. 3) fluid in the barrel 30 is forced through the end 31 of the barrel 30. On the other hand, when the plunger 21 is drawn out of the barrel 30, fluid is drawn in to the barrel 30 through the end 31. In FIG. 3 the end 31 of the barrel is shown as completely open, but in alternative constructions it can be partially closed, containing an orifice for example. The plunger barrel 30 is preferably rigid and may be made of a plastics material for ease of manufacture and cost effectiveness, and is preferably an easily mouldable plastics material such as polycarbonate (PC) or poly(methyl methacrylate) (PMMA). For a fluidics or nanopore application, the pump can have a barrel volume of 10 ml or less, optionally 5 ml or less, further optionally 2 ml or less, and still further optionally 1 ml or less. The rigidity of the barrel may be determined by the choice of barrel material or by the thickness of the barrel 30. The rigidity may be provided or enhanced by surface features on the outer side of barrel 30, such as a screw thread.

As previously discussed, conventional syringe pumps commonly seal the plunger against the barrel with an elastomeric seal such as an O-ring. Such an O-ring is provided around the outside of plunger, and is conventionally in contact with the fluid in the barrel. When emptying the pump, the seal helps prevent fluid from flowing around the plunger rather than through the orifice in the barrel. When filling the pump by drawing fluid through the orifice, the seal helps reduce air from the pump surroundings being drawn into the barrel around the plunger and so ensures that fluid is drawn in through the orifice.

Figure 2:
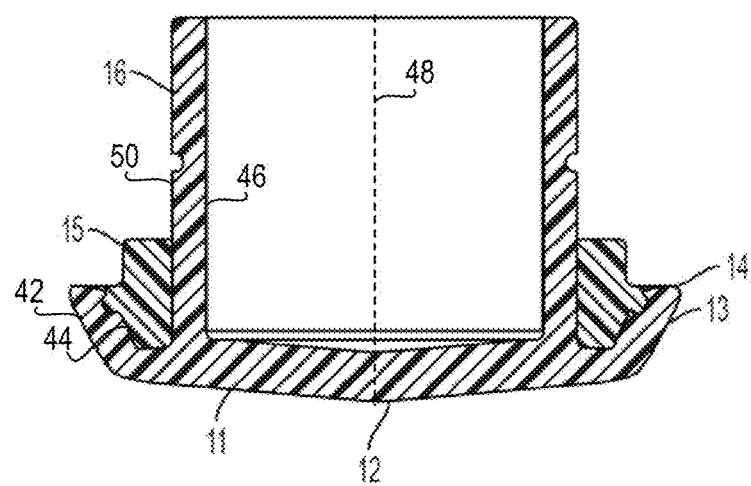
FIG. 2 is a cross-sectional view of the piston seal of FIG. 1.

The piston head 10 of FIG. 4 is shown in detail in FIGS. 1 to 3. In contrast to conventional pistons, the piston head 10 has a piston seal that seals against the barrel 30 differently.

In the Figures, the piston head 10 fits to the end of the plunger 21, a ridge on an inner surface of the plunger clipping over the depression 17 formed in the piston head. However, any suitable method of attaching the piston head 10 to a plunger 21 may be used. Alternatively, the piston head 10 might not be separate to the plunger 21; that is, the piston head 10 can be formed integrally with the body of the plunger 21 itself.

The piston head 10 has piston seal comprising a barrier portion 11 that forms a barrier across the barrel 30. The barrier portion 11 has a barrier surface 12 that faces the fluid being displaced within the barrel (whether that fluid is being driven out of the barrel 30 or drawn into the barrel 30).

The peripheral portion of the barrier portion 11 (that is, the radially outermost portion) is formed into a lip 13, which projects from the opposite side of the barrier portion 11 to the barrier surface 12. In the figures, the lip 13 stands proud from the upper surface of the barrier portion 11, projecting upwards whilst the barrier surface (which contacts the liquid in the syringe barrel) faces downwards. That is, the lip 13 is formed by the edge of the barrier portion 11 retreating back in the direction of the plunger 21 and away from the base 31 of the barrel 30. As such, the lip 13 extends and projects at least partially around resilient member 15 (discussed in more detail below). However, the lip 13 still at least partially extends outwards in a radial direction from the centre of the pump head 10. As such, the barrier surface 12 has a slightly convex shape with respect to the barrel chamber 33 (i.e. a convex shape when the barrier surface 12 is viewed directly), especially in the vicinity of the inner surface 34 of the barrel 30 and the point at which the lip 13 merges into the bulk of the barrier portion 11.

The widest diameter of the piston seal occurs on the outer surface 42 of the lip 13 (i.e. the continuation of the barrier surface 12). For fluidics or nanopore applications, the widest outer diameter of the piston seal may be 50 mm or less, optionally 25 mm or less, and still further optionally 15 mm or less. In a preferred embodiment, the outer diameter is 11.6 mm. Further, the outer diameter may be 1 mm or more, optionally 3 mm or more, further optionally 5 mm or more and still further optionally 10 mm or more. At rest, when the piston head 10 is not assembled into a corresponding barrel 30, this widest diameter of the pump seal is wider than the inner diameter of the barrel 30. As such, when the pump head 10 is inserted into the barrel 30, the lip 13 is deflected inwardly (i.e. towards the centre of the pump head). That is, the pump head 10 deforms to allow insertion into the barrel 30.

The barrier portion 11 of the pump head 10 is preferably sufficiently rigid, such that it will resist the deflection of the lip 13 and hence force the lip 13 against the barrel 30 and form a seal around the piston head 10. The barrier portion may be made of plastic or a material other than plastic, such as a metal. However metals are generally too inflexible to be suitable and are generally not preferred, unless provided for example as a thin layer or coating on the resilient member. Another reason plastics might be preferred over metals would be if there are concerns regarding metals reacting with or contaminating the fluid being pumped. For example, in lab-on-a-chip applications, such as nanopore applications, it is desirable to minimise fluid contamination and so plastics materials are often more suitable for constructing fluidic and microfluidic circuits than metals. Similarly, to avoid contamination when using plastics for the piston head 10 it is preferable to use plastics which exhibit low chemical/plasticiser leaching. Preferable plastics include polytetrafluoroethylene (PTFE), ultra-high-molecular-weight polyethylene (UHMWPE), polypropylene (PP), high density polyethylene (HDPE), perfluoroalkoxy (PFA) or fluorinated ethylene propylene (FEP).

However, the use of rigid materials such as plastics for the barrier portion 11 has a potential drawback relating to the durability of the seal. Over time, once the piston head 10 has been positioned in the barrel 30, the material of the barrier portion might exhibit creep in the region of the lip 13. That is, the material might begin to deform to take the shape of the barrel 30, decreasing the force pushing the lip 13 against the inner wall 34 of the barrel. As this process occurs, the quality of the seal around the piston head 10 will decrease. This drawback is alleviated by the presence of the resilient member.

The quality of the seal around the piston head 10 is particularly important in lab-on-a-chip applications such as nanopore applications. This is because such applications operate with very small volumes of fluid and so it is important that the amount of fluid being dispensed by a pump is dispensed as accurately as possible. The introduction of a weak seal in a pump reduces the accuracy of dispensing because fluid can leak around the plunger 21 instead of exiting the pump 1 through the orifice 31, without the operator's knowledge. As such, an experiment would proceed with the operator assuming a certain amount of fluid had been dispensed, when in fact a different amount had been dispensed.

Further, when charging the pump 1 by drawing fluid in through the orifice 31 a weak seal can cause a similar problem: instead of drawing in fluid, air from the pump surroundings can enter the barrel chamber 33 around the plunger 21 instead of fluid being drawn into the chamber 33 via the end of the barrel 31. Once again, the operator would not be aware of this, and so would assume a certain amount of fluid had been charged to the pump 1, when in fact a lesser amount had been charged.

The pump 1 at least partially overcomes these problems by the provision of a resilient member 15 behind the lip 13.

That is, the resilient member 15 is provided on the opposite side of the barrier portion 11 to the barrier surface 12, and inside (i.e. closer to the centre of the piston head 10) the lip 13. The lip 13 thus projects at least partially around the resilient member 15. The retaining portion 16 comprises an inside surface 46 proximal to a central axis 48 of the piston head and an outer surface 50 distal to the central axis 48 of the piston head. That is, as shown in the Figures, the lip 13 can extend around the resilient member 15, whilst part of the resilient member 15 can extend further away from the barrier portion 11 than the lip 13, in the axial direction of the piston, along the outer surface 50 of the retaining portion 16. Increasing the distance that the resilient portion 15 extends along the outer surface 50 of the retaining portion 16 increases the surface area provided between the two sections and thus increases the strength of any bond between the two sections.

The resilient member 15 can be made of a different material to the barrier portion 11. The resilient member 15 can be an elastomeric material which resists compression and therefore the deformation of lip 13 as the plunger 21 is inserted into the barrel 30. As such, even if the barrier portion 11 and/or lip 13 is subject to material creep, the resilient member 15 will continue to resist its own compression and force the lip 13 back towards the inner wall 34 of the barrel 30. This maintains a good seal.

If the force resisting the deformation of the lip 13 is too strong, the pump 1 can become difficult to actuate. That is, if the lip 13 is pushed against the barrel 30 too strongly, it can become difficult to move the plunger 21 within the barrel, making the pump 1 stiff to operate. To prevent the pump 1 becoming too stiff, the lip 13 can be reduced in thickness. Reducing the thickness of the lip 13 reduces the hoop stresses in the lip 13 as it is deformed, and hence reduces the force with which the lip 13 resists deformation.

However, reducing the lip 13 thickness has an associated potential disadvantage that an overly thin lip 13 could be easily damaged, during either operation or assembly for example. If a lip 13 is too thin, any damage could lease to an incomplete seal being formed, and thus prevent the pump 1 working properly.

Therefore, rather than reducing the thickness of the entire lip 13 uniformly, it can be preferable to shape the lip to be tapered so as to thin towards the outer end of the lip 13. That is, the thickness of the lip 13 can varied to be thinner at the tip of the lip 13 and thicker where the lip joins the barrier portion 11. The tapering construction allows for a mechanically strong lip to be formed, which is resistant to damage and which also allows for a reduction in hoop stress in the region of the lip 13 towards the tip that will be deformed when the piston head 10 is inserted in the barrel 30.

The resilient member 15 can be elastic, such as a metal spring or an elastomeric material such as a silicone or a thermoplastic elastomer (TPE). One advantage of the construction of the piston head 10 is that, as long as the seal is functioning, the resilient member 15 does not come into contact with the fluid being pumped in and out of the chamber 33. As such, there is no direct contamination of the fluid by contacting the resilient member 15. However, as discussed above the use of metal may be undesirable in certain applications. Further, the use of elastomeric materials, such as a rubber, may be preferred to assist in simplifying the manufacture of the piston head 10. For example, two-shot moulding could be used when employing an elastomeric resilient member.

Another advantage of the construction of the piston head 10 is that the resilient member does not come into contact with the inner surface 33 of the barrel 30. This is advantageous because it results in the contact between the plunger 21 and the barrel 30 occurring only around the lip 13 of the piston head 10. Since both the barrel 30 and the lip 13/barrier portion 11 are made of plastics materials the friction between the surfaces will be relatively low, compared to a convention syringe plunger seal in which the contact (and seal) occurs between the barrel and the elastic material of the sealing O-ring.

For example, Table 1 shows the typical dynamic coefficient of frictions for some generic plastics materials relative to steel measured in accordance with the industry standard method ASTM D1894. In some cases, the coefficient of dynamic friction of PTFE relative to steel, measured according to ASTM D1894 can be 0.05 to 0.16. In some cases, the coefficient of dynamic friction of polypropylene relative to steel, measured according to ASTM D1894 can be 0.2 to 0.4. In some cases, the coefficient of dynamic friction of ETFE relative to steel, measured according to ASTM D1894 can be 0.3 to 0.74. In some cases, the coefficient of dynamic friction of PMMA relative to steel, measured according to ASTM D1894 can be 0.15 to 0.8. Preferable materials for the barrier portion and the barrel have a coefficient of dynamic friction relative to steel of 0.4 or less, preferably 0.2 or less, measured in accordance with ASTM D1894.

TABLE 1

Typical coefficients of dynamic friction of some materials

| Material | Coefficient of Dynamic Friction |
|---|---|
| UHMWPE | 0.1-0.2 |
| PTFE | 0.05-.1 |
| FEP | 0.08-.3 |
| Polypropylene | 0.3-0.4 |
| HDPE | 0.07-0.4 |
| Ethylene tetrafluoroethylene (ETFE) | 0.3-0.4 |
| PMMA | 0.5-0.8 |
| Polycarbonate | 0.3-0.9 |
| Nylon | 0.2-0.5 |
| Acetal | 0.1-0.4 |
| Acrylonitrile butadiene styrene (ABS) | 0.2-0.5 |
| NexPrene (RTM) thermoplastic vulcanizates | 0.4-0.5 |

However, as can be seen from the table, plastics can have higher coefficients of friction. In particular, softer materials more commonly used as seal materials are likely to have higher coefficient of friction. For example, the coefficient of friction of silicone rubber is anecdotally close to 1, and special materials (such as NexPrene (®) listed in Table 1) have been developed to try and obtain similar elastomeric properties to silicone whilst exhibiting lower coefficients of friction that silicone. However, as shown in Table 1, the coefficient of friction of materials such as NexPrene is not as low as materials such as PTFE or UHMWPE for example.

As a result, the piston seal of the invention can reduce occurrence of stick-slip when the pump is driven by using materials to form the seal that are not conventionally suitable. This is due to the different construction of the seal, compared to conventional seals, which provides a resilient or energised seal without bringing the material providing resilience into contact with the barrel. This results in both a smoother pumping operation and also a lower driving force being required to actuate the pump. This in turn results in lower pressures in the pump chamber 33 and so smaller amounts of air compression and more accurate dispensing.

Another way of lowering the friction between the piston and the barrel is to provide a suitable surface treatment on either the barrel, the piston, or both. The surface treatment can introduce a texture that reduces the overall area of contact between the piston and the barrel, and thus the friction acting between those surfaces. On the other hand, the surface is preferably not textured so much as to compromise the quality of the seal. As such, the ideal surface finish may be material dependent.

However, whilst UHMWPE and PTFE for example have low coefficients of friction, they exhibit significant creep. The provision of a resilient elastic member having a lower creep than the material of the peripheral section of the piston seal removes or reduces the tendency of the sealing surface to creep over time, advantageously providing a piston seal with a low coefficient of friction which is able to maintain a good seal over time against a piston barrel.

As such, the piston head 10 provides a strong lasting seal by the provision of the resilient member 15 behind the lip 13, whilst also avoiding the pump becoming too stiff to actuate smoothly and accurately. This allows for the accurate dispensing of fluid at low flow rates, such as in the range of from 1 μl/s to 0.1 μl/s. To provide these flow rates, a piston head diameter (and corresponding barrel size) of 50 mm or less, optionally 20 mm or less, and further optionally 15 mm or less can be used in a system with appropriately precise control of the longitudinal displacement of the head 10.

The resilient member 15 is positioned between the lip 13 and the retaining portion 16 of the piston head 10. As such, the resilient member is compressed against the retaining portion 16 when the lip 13 is pushed back, and this can hold the resilient member 15 in place. However, it can be preferable to further secure the resilient member 15 in place, to avoid it working loose during use. For example, the resilient member may be attached to the barrier portion 11 or the restraining member 16 by chemical means such as an adhesive. Alternatively, or in combination with an adhesive, the piston head can be shaped to mechanically hold the resilient member 15 in place. As can be seen in FIG. 2, the inside surface 44 of the lip 13 is shaped to have an overhang 14 which projects radially inwards and above the surface immediately below it. This allows for a resilient member 15 to be positioned under the overhang 16, and thus secured in place by the overhang 16 acting as a physical blockage to the resilient member 15 moving out of place. This effect is increased as the lip 13 is deformed inwardly, moving the overhang further inwards.

The barrier portion 11 and the retaining portion 16 can be made of a plastics material and preferably for nanopore applications uses a plastics material that exhibits low chemical/plasticiser leaching. Possible plastics include polytetrafluoroethylene (PTFE), ultra-high-molecular-weight polyethylene (UHMWPE), polypropylene (PP), perfluoroalkoxy (PFA) or fluorinated ethylene propylene (FEP).

UHMWPE is a preferable material for forming the barrier portion 11 and resilient member 16 because is exhibits a relatively low amount of creep compared to PTFE, whilst also being mouldable.

Moulding is a preferred manner of producing the piston head 10, because it is allows mass manufacture of substantially identical products. Further, moulding enables the formation of the resilient member 15 within the lip 13 in a way that ensures that the resilient member fills the available space and is securely positioned (e.g. under any overhangs). A moulding process may include first moulding the barrier portion 11/retaining portion 16 as an integrated structure that includes all the features of the lip 13, using a plastics material such as UHMWPE. Thereafter, in a second moulding step, the resilient member 15 may be formed by moulding the resilient member 15 into the region between the lip 13 and the retaining portion 16. As such the material used to form the resilient member (TPE for example) will flow under any overhangs 16, for example, before setting in position.

Such a two stage process not only produces a good fit between the resilient member 15 and the rest of the piston head 10, but also produces a good bond between the two sections. The moulding can be carried out as part of two-stage over-moulding process, using different tools for each moulding step. Alternatively, the bond between the two sections can be further improved by using a two-shot moulding process that utilises the same tool for both moulding operations. A two-shot moulding process preferably allows for the formation of the resilient member 15 without exposing the material of the resilient member 15 on the barrier surface 12. For example, the material for the resilient member 15 can be injected into position through the retaining portion 16 or through the barrier portion 11 from the piston side (using channels to allow the material to pass through the barrier portion 11 to behind the lip 13 at the periphery of the barrier portion 11).

The barrier portion may be a single material, the material having the properties as mentioned above. Alternatively, the barrier material may be made from two or more materials wherein the sealing surface of the barrier portion is made from the above-mentioned material and a part of the barrier portion which is not intended to contact the barrel is made of one or more other materials.

The present invention has been described above with reference to specific embodiments. It will be understood that the above description does not limit the present invention, which is defined in the appended claims.

The invention claimed is:

1. A piston head, comprising:
   i) an integrated structure that comprises a barrier portion, a retaining portion comprising an inside surface proximal to a central axis of the piston head and an outer surface distal to the central axis of the piston head, and a lip; and
   ii) a separate resilient member,
   wherein the resilient member is made of a material having a lower elastic modulus than the material of the integrated structure,
   wherein the integrated structure is configured to directly connect to a piston,
   wherein the lip projects from the barrier portion, so as to define an available space between the lip and the outer surface of the retaining portion,
   wherein the retaining portion is configured for retaining the resilient member against the lip,
   wherein the resilient member is positioned so as to fill the available space between the lip and the retaining portion and to resist inwards deformation of the lip, and
   wherein an inner surface of the lip comprises an overhang and the resilient member projects beneath the overhang.

2. The piston head according to claim 1, wherein the lip is tapered such that a thickness of the lip decreases from a point where the lip joins the barrier portion to a tip.

3. The piston head according to claim 1, wherein the resilient member is made of a material that is different than a material of which the barrier portion is made.

4. The piston head according to claim 1, wherein the resilient member is subject to a lower creep than the lip.

5. The piston head according to claim 1, wherein the barrier portion is made of a plastics material having a dynamic coefficient of friction of less than or equal to 0.4 as measured relative to steel.

6. A piston head, comprising:
   i) an integrated structure that comprises a barrier portion, a retaining portion comprising an inside surface proximal to a central axis of the piston head and an outer surface distal to the central axis of the piston head, and a lip; and
   ii) a separate resilient member,
   wherein the resilient member is made of a material having a lower elastic modulus than the material of the integrated structure,
   wherein the integrated structure is configured to directly connect to a piston,
   wherein the lip projects from the barrier portion, so as to define an available space between the lip and the outer surface of the retaining portion,
   wherein the retaining portion is configured for retaining the resilient member against the lip,
   wherein the resilient member is positioned so as to fill the available space between the lip and the retaining portion and to resist inwards deformation of the lip, and
   wherein the resilient member is bonded to the lip and/or the retaining portion.

7. The piston head according to claim 6, wherein the resilient member is bonded to the lip and the retaining portion.

8. A method of forming a piston seal, the method comprising:
   i) molding an integrated structure that comprises a barrier portion, a retaining portion comprising an inside surface proximal to a central axis of the piston head and an outer surface distal to the central axis of the piston head, and a lip, wherein the integrated structure is configured to directly connect to a piston;
   ii) molding a separate resilient member that is made of a material having a lower elastic modulus than the material of the integrated structure; and
   arranging the barrier portion and the retaining portion and the resilient member to form the piston seal, such that i) the lip projects from the barrier portion, so as to define an available space between the lip and the outer surface of the retaining portion, ii) the retaining portion is configured for retaining the resilient member against the lip, and iii) the resilient member is positioned so as to fill the available space between the lip and the retaining portion and to resist inwards deformation of the lip.

9. The method according to claim 8, wherein the steps of molding the integrated structure and molding the resilient member are performed as an over-molding or two-shot molding process.

10. A piston head, comprising:
    i) an integrated structure that comprises a barrier portion, a retaining portion comprising an inside surface proximal to a central axis of the piston head and an outer surface distal to the central axis of the piston head, and a lip; and ii) a separate resilient member, wherein the resilient member is made of a material having a lower elastic modulus than the material of the integrated structure, wherein the integrated structure is configured to directly connect to a piston, wherein the lip projects from the barrier portion, so as to define an available space between the lip and the outer surface of the retaining portion, wherein the retaining portion is configured for retaining the resilient member against the lip, wherein the resilient member is positioned so as to fill the available space between the lip and the retaining portion and to resist inwards deformation of the lip, and , wherein the resilient member extends further away from the barrier portion than the lip, in an axial direction, along the retaining portion.

* * * * *

UNITED STATES PATENT AND TRADEMARK OFFICE
CERTIFICATE OF CORRECTION

PATENT NO.         : 10,675,412 B2
APPLICATION NO.    : 14/344463
DATED              : June 9, 2020
INVENTOR(S)        : Anthony Jones et al.

It is certified that error appears in the above-identified patent and that said Letters Patent is hereby corrected as shown below:

On the Title Page

In the Abstract, Column 2:
"A piston head for a syringe pump comprises a barrier portion (11) for driving fluid through a syringe pump barrel (30), wherein a peripheral section (13, 14) of the barrier portion (11) is shaped to seal against the syringe pump barrel (30); and a re-silent member (15) arranged to resist deformation of the shaped peripheral section (13, 14) of the barrier portion (11)."

Should be replaced with:
"A piston head for a syringe pump comprises a barrier portion (11) for driving fluid through a syringe pump barrel (30), wherein a peripheral section (13, 14) of the barrier portion (11) is shaped to seal against the syringe pump barrel (30); and a resilient member (15) arranged to resist deformation of the shaped peripheral section (13, 14) of the barrier portion (11)."

Signed and Sealed this
Tenth Day of November, 2020

Andrei Iancu
*Director of the United States Patent and Trademark Office*